United States Patent
Fitamen et al.

(10) Patent No.: US 7,611,901 B2
(45) Date of Patent: Nov. 3, 2009

(54) METHOD FOR DETERMINING THE CONTENT OF DIESEL FUEL IN A LUBRICATING OIL OF A COMBUSTION ENGINE

(75) Inventors: Eric Fitamen, Fontenay Aux Roses (FR); Laurent Tiquet, Gallardon (FR)

(73) Assignee: Renault S.A.S., Boulogne (FR)

( * ) Notice: Subject to any disclaimer, the term of this patent is extended or adjusted under 35 U.S.C. 154(b) by 0 days.

(21) Appl. No.: 12/092,617

(22) PCT Filed: Oct. 26, 2006

(86) PCT No.: PCT/FR2006/051111

§ 371 (c)(1),
(2), (4) Date: Aug. 27, 2008

(87) PCT Pub. No.: WO2007/051941

PCT Pub. Date: May 10, 2007

(65) Prior Publication Data

US 2009/0029475 A1      Jan. 29, 2009

(30) Foreign Application Priority Data

Nov. 3, 2005      (FR) .................................. 05 11195

(51) Int. Cl.
*G01N 33/30* (2006.01)
*G01N 30/02* (2006.01)

(52) U.S. Cl. .................. 436/60; 436/139; 436/141; 436/161; 702/22; 702/23; 702/32; 73/19.02; 73/23.22

(58) Field of Classification Search .................... 436/60, 436/139, 141, 143, 161; 422/89; 702/22, 702/23, 32; 210/656; 73/19.02, 23.22
See application file for complete search history.

(56) References Cited

U.S. PATENT DOCUMENTS

2003/0194811 A1    10/2003 Reischman et al.

OTHER PUBLICATIONS

Ruppel et al. Perkin Elmer Field Application Report, Gas Chromatography, "A Novel Method for High-Speed Determination of Fuel Diluents in Lubricating Oils", 2005, pp. 1-3.*
Anonymous, "Standard Test Method for Diesel Fuel Diluent in Used Diesel Engine Oils by Gas Chromatography[1]", ASTM International, Designation: D 3524-04, pp. 1-6, 2004. XO009067885.
Anonymous, "Determination of Readily Volatile Components in Used Automotive Engine Oils by Gas Chromatography", DIN 51380, pp. 1-2, 1990. XP009068152.

* cited by examiner

*Primary Examiner*—Maureen M Wallenhorst
(74) *Attorney, Agent, or Firm*—Oblon, Spivak, McClelland, Maier & Neustadt, L.L.P.

(57) ABSTRACT

A method for determining proportion of diesel fuel in a lubricating oil of a combustion engine, including: forming a mixture containing an oil sample and a $C_5$ hydrocarbon such as a $C_5$ alkane; injecting the mixture into the injector of a gas chromatograph; establishing a chromatograph of the sample; determining a first parameter M representative of the area of a peak associated with the $C_5$ hydrocarbon such as a $C_5$ alkane; determining a second parameter C representing of the area of at least one peak associated with a hydrocarbon representative of diesel fuel; and determining the proportion T of diesel fuel by a formula $$T = \frac{C/(M) - b}{a}$$

in which a and b are constants defining equation y=ax+b of a calibration straight line of the ratio between the second and the first parameters as a function of the proportion of diesel fuel.

8 Claims, 2 Drawing Sheets

METHOD FOR DETERMINING THE CONTENT OF DIESEL FUEL IN A LUBRICATING OIL OF A COMBUSTION ENGINE

The invention relates to the analysis of lubricating oils, and in particular to the determination of the content of fuel in the oil of an internal combustion engine.

Methods for analyzing the content of diesel fuel in a lubricating oil are known but are not entirely satisfactory, in particular with regard to the accuracy of the result of the analysis. This is because it is difficult to differentiate between the diesel fuel which comprises predominantly saturated and unsaturated $C_6$ to $C_{25}$ hydrocarbons, and the lubricating oil which comprises predominantly saturated and unsaturated $C_{20}$ to $C_{50}$ hydrocarbons. A very high degree of reliability of the results is required, in particular for the development of engines equipped with particle filters.

The invention aims to solve several of these drawbacks. The invention thus proposes a method for determining the proportion of diesel fuel in a lubricating oil of a combustion engine, comprising the following steps:

forming a mixture containing a sample of lubricating oil to be analyzed and a $C_5$ hydrocarbon such as a $C_5$ alkane according to the predetermined proportion;

injecting the mixture into the injector of a gas chromatograph;

establishing a chromatogram of the sample to be analyzed;

determining a first parameter M representative of the area of a peak of the chromatogram associated with the $C_5$ hydrocarbon such as a $C_5$ alkane;

determining a second parameter C representative of the area of at least one peak of the chromatogram associated with a hydrocarbon representative of the diesel fuel;

determining the proportion T of diesel fuel of the sample to be analyzed, by the following formula:

$$T = \frac{C/(M) - b}{a}$$

with a and b being constants defining the equation y=ax+b of a calibration straight line of the ratio between the second and the first parameters as a function of the proportion of diesel fuel.

Other features and advantages of the invention will emerge clearly from the description which is given thereof hereinafter, by way of indication that is in no way limiting, with reference to the attached drawings, in which.

The invention proposes to determine the content of diesel fuel in a sample of a lubricating oil of an internal combustion engine. For this, a mixture containing a sample of lubricating oil to be analyzed and a $C_5$ hydrocarbon such as a $C_5$ alkane, in a predetermined proportion, is formed. A sample is injected into the chromatograph and a chromatogram of the sample is produced. A parameter representative of the area of the peak of the $C_5$ hydrocarbon is determined, as is a parameter representative of a peak associated with a hydrocarbon representative of the diesel fuel. Based on calibration data for these parameters, the content of diesel fuel in the sample is determined.

In the patent application, the term "$C_n$ hydrocarbon" refers to a family of isomeric compounds with n greater than 5.

Figure 1:
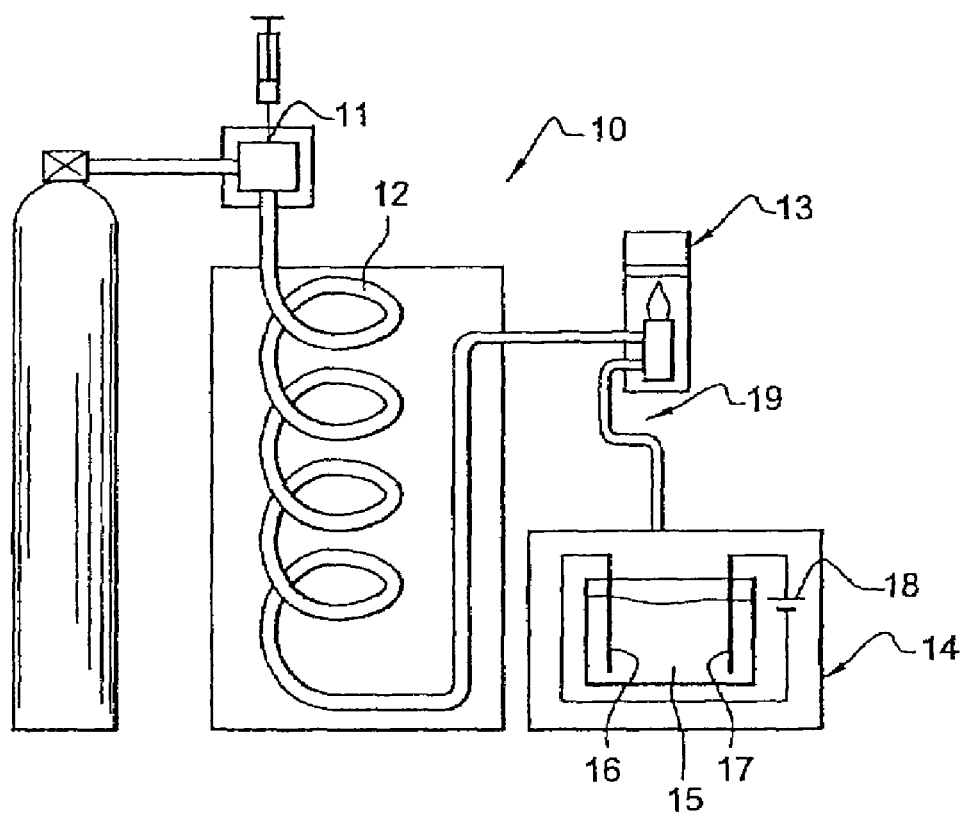
FIG. 1 illustrates schematically a chromatograph according to the prior art.

FIG. 1 illustrates a known chromatograph of the prior art. The chromatograph 10 comprises an injector 11 for products to be analyzed, a separating column 12 for separating the products to be analyzed, a detector 13 of said products and a device 14 for producing combustion gas.

The various compounds of the products to be analyzed pass through the separating column 12 in different amounts of time. The detector 13 is, for example, a flame ionization detector known to those skilled in the art, and has a flame fed by the gases originating from the device 14. This device 14 has, for example, a reservoir of distilled water and an electrolysis device 15 containing distilled water in which two electrodes 16 and 17 are immersed. These electrodes are supplied by an electric power source 18. Hydrogen and oxygen form at the electrodes and supply the flame ionization detector with oxygen and hydrogen via a pipe 19. The detector 13 also receives a gas for transporting the products in the separating column, for example hydrogen, helium or nitrogen. The detector 13 measures an intensity generated during the combustion of a compound derived from the column 12. The intensity generated varies according to the presence or absence of a compound in the chamber. A chromatogram is generated so as to represent, for example, the intensity as a function of time.

The invention proposes to form a mixture containing a sample of lubricating oil to be analyzed and the $C_5$ hydrocarbon such as a $C_5$ alkane according to predetermined proportions. The mixture is injected into the chromatograph injector. A chromatogram of the sample to be analyzed is established. A first parameter representative of the area of a peak associated with the $C_5$ hydrocarbon is determined. A second parameter representative of the area of at least one peak associated with a hydrocarbon representative of the diesel fuel is also determined. The proportion T of diesel fuel of the sample to be analyzed is calculated by the following formula:

$$T = \frac{C/(M) - b}{a}$$

a and b being constants defining the calibration straight line of the chromatograph, generally defined by C/M=a×T+b. The parameters are, for example, proportional to the amplitudes or to the areas of the peaks of the chromatogram.

The second parameter may, for example, be a function of the height or of the area of a peak associated with a hydrocarbon belonging to the $C_6$ to $C_{25}$ group.

It is possible to envision calculating, beforehand, an approximation of the content of diesel fuel by taking into account a second parameter which is a function only of the peak of the $C_{20}$ hydrocarbon. According to this approximation, it is then possible to determine the peaks of which of the hydrocarbons will be taken into account in the parameter C, in order to calculate the content of diesel fuel. The number of peaks taken into account may thus be a function of the approximation calculated.

Advantageously, the second parameter may be representative of the area of several peaks associated with respective hydrocarbons belonging to the $C_{20}$ to $C_{25}$ group.

In order to take account of a relative area of the various compounds for various chromatographic conditions, the coefficient C is advantageously corrected so as to relate the concentration of the $C_5$ compound to a desired value. C may in particular be determined by the following formula: $C=\alpha \cdot C0/[C_5]$ C0 being the area of the peak associated with the $C_5$ hydrocarbon such as a $C_5$ alkane, a being a coefficient of correction to a reference concentration and $[C_5]$ being the concentration of the $C_5$ hydrocarbon in the sample.

The mixture formed may comprise a predetermined proportion of carbon disulfide. The function of the carbon disulfide is to dilute the entire oil+$C_5$ mixture in order to mix them homogeneously and to have a liquid and fluid medium, the separation of which is facilitated. Moreover, the carbon disulfide is advantageously invisible to the detector, even in a large amount. The carbon disulfide does not therefore disturb the detection of the diesel fuel and of the oil.

The calibration straight line is preferably prepared beforehand with the same type of diesel fuel and the same type of oil as in the sample to be analyzed.

For the prior determination of the calibration straight line equation, the following steps can be carried out. Several standard mixtures comprising a lubricating oil and diesel fuel according to distinct predefined proportions, and $C_5$ hydrocarbon such as a $C_5$ alkane according to a predetermined proportion, are formed. The diesel fuel content of a standard sample will subsequently be noted T0. For each standard mixture:

the standard mixture is injected into the injector of a gas chromatograph;

a chromatogram of the standard mixture is established;

a first parameter M0 representative of the area of a peak of the chromatogram associated with the $C_5$ hydrocarbon such as a $C_5$ alkane is determined;

a second parameter C0 representative of the area of a peak of the chromatogram associated with a hydrocarbon representative of the diesel fuel is determined.

The constants a and b are determined from the pairs of parameters obtained for the various mixtures obtained (which may be represented by points of the x-axis T0 and of the y-axis C0/M0). The constants a and b are, for example, obtained by taking, as calibration straight line, the straight line which corresponds best to the various pairs formed.

The chromatogram may be established using a flame ionization detector, it being possible for a calculation member to perform integrations of the chromatogram in order to calculate the area of each pic.

An example of conditions for carrying out the method according to the invention will now be given in detail.

The following apparatus can be used:

a gas chromatograph, preferably providing precise programming and adjustment of the temperature and the pressure in the column. The chromatograph is advantageously fed with helium, air of industrial quality and hydrogen of N55 quality;

an apolar capillary column sold by the company Chrompack under the reference CP Syl 19 cb, which is 10 meters in length and 0.53 mm in diameter, with a film thickness of 1 µm;

a 2-meter precolumn devoid of silica, equipped with a glass union piece forming a junction with the capillary column;

a flame ionization detector (FID);

an integration device in the form of a computer running the software sold under the reference HPCHEM in a version subsequent to A.04.02;

a cold on-column injector advantageously providing pressure adjustment and an automated injection device having at least 8 positions, a 100-position changer being recommended;

a balance with a precision of 0.1 mg;

a vibrating table for agitating and homogenizing the samples.

The following reactants can be used:

carbon disulfide ($CS_2$), such as that sold by the company Prolabo with Normapur analytical quality;

pentane ($C_5$) having a purity of greater than 99%;

commercial diesel fuel with no additives;

a fresh oil of ALEA A2/B2 15W40 type.

The following standard samples may be used. Fresh oil/diesel fuel mixtures are prepared and have the following respective proportions, by mass, of diesel fuel: 1, 2, 3, 4, 5, 6, 7, 8, 10, 12 and 15%.

In order to increase the accuracy of the calibration, it is preferable to use, for these standards, a fresh diesel fuel and a fresh oil, which correspond respectively to the diesel fuel and to the oil that were used to obtain the samples to be analyzed.

For each standard sample, the following preparation steps are carried out:

the weight of oil corresponding to its titration by weight is sampled into a flask and weighed. Its weight will be noted $m_1$;

the volume of diesel fuel required to obtain its titration by weight is sampled and placed in the flask. The weight of the oil-diesel fuel mixture will be noted $m_2$;

the mixture is vigorously shaken for at least 10 minutes with a vibrating table so as to homogenize it.

The standard samples then undergo the process described below for the samples to be analyzed.

For each sample of oil to be analyzed, the following preparation steps are carried out:

1.7 ml of the sample to be analyzed are sampled and then weighed. The weight of this sample will be noted $m_3$. Optionally, a further sample is taken if the weight does not correspond to a range of expected values;

20 µl of pentane are added to the sample to be analyzed. The pentane is stored and sampled at ambient temperature. The weight of the mixture obtained will be noted $m_4$;

the mixture is virtually immediately diluted by adding 5 ml of carbon disulfide ($CS_2$), the flask containing the mixture obtained is hermetically sealed virtually immediately in order to limit evaporation of the $CS_2$ solvent;

the mixture obtained is agitated by means of a vibrating table for approximately 1 minute so as to homogenize the mixture. The mixture then obtained is thus diluted to 75% by volume in the $CS_2$ and is ready to be injected into the chromatograph;

optionally, in order to increase the storage time of the mixture obtained, the latter is poured into a 2 ml microfiol so as to guarantee as small a dead volume as possible. A hermetic cap may be crimped over the opening of the microfiol. As many microfiols as necessary for a given mixture to be analyzed are filled;

0.5 µl is injected by means of the automatic injector.

The volumes and weights are of course given only by way of indication, it being possible for other values to be used by those skilled in the art.

Figure 2:
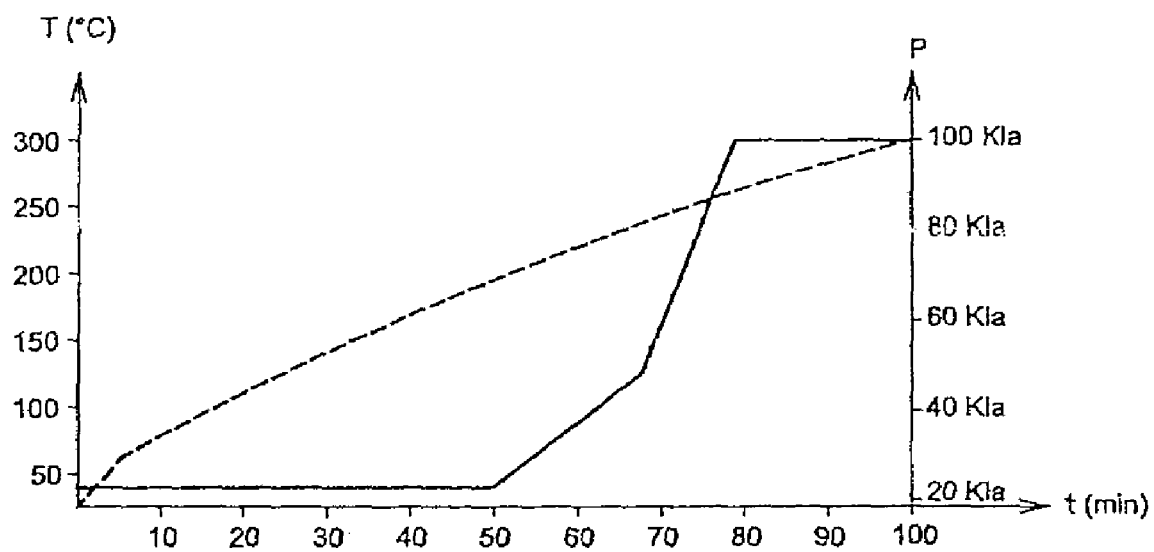
FIG. 2 illustrates examples of parameters of the chromatograph used in the context of the invention.

An example of chromatographic analysis will now be described in detail. During this analysis, the carrier gas in the separating column is helium. Chromatograph oven temperature and helium pressure programs can impose the diagrams illustrated in FIG. 2. The temperature of the injector is controlled so as to track the temperature program 10° C. in advance, according to the oven track principle. The flow rate of the carrier gas in the column is conditioned by that imposed by the helium pressure program. The chromatograph operates by pressure adjustment.

For the chromatograph used by the applicant during its tests, the flow rate of hydrogen in the detector was approximately equal to 30 ml/min and the flow rate of air in this detector was equal to 400 ml/min, to within 10 ml/min.

For the integration of the peaks of the various compounds, the following periods were used in the chromatography cycle:

the integration of the pentane standard part was carried out between t=22 seconds and t=33 seconds;

the integration of the carbon disulfide ($CS_2$) part was carried out, excluding $C_{20}$, between t=33 seconds and t=37 minutes and 40 seconds. The compounds between $C_5$ and $C_{20}$ exclusive belong to the diesel fuel;

the integration between the compounds of the diesel fuel part $C_{20}$ and $C_{22}$ exclusive was carried out between t=37 minutes and 40 seconds and t=44 minutes and 15 seconds;

the integration between the compounds of the diesel fuel part $C_{22}$ and $C_{24}$ exclusive was carried out between t=44 minutes and 15 seconds and t=51 minutes and 15 seconds;

the integration between the compounds of the diesel fuel part $C_{24}$ and $C_{25}$ exclusive was carried out between t=51 minutes and 20 seconds and t=54 minutes and 20 seconds;

the integration between the oil part from $C_{25}$ was carried out between t=54 minutes and 20 seconds and t=97 minutes.

Advantageously, the integration times for the various compounds are adjusted according to the aging of the column.

The chromatograms obtained are analyzed in order to extract the areas of the peaks associated with the various compounds. Taking A0 to be the area extracted for the pentane standard, A1 is the area associated with carbon disulphide, A2 is the area associated with up to $C_{20}$ exclusive, A3 is the area associated with up to C22 exclusive, A4 is the area associated with up to C24 exclusive and A5 is the area associated with up to C25 exclusive.

Advantageously, the concentration of pentane standard is related to an imposed value. An area relating to the various compounds (or family of compounds) may thus be calculated, irrespective of the chromatographic conditions.

Figure 3:
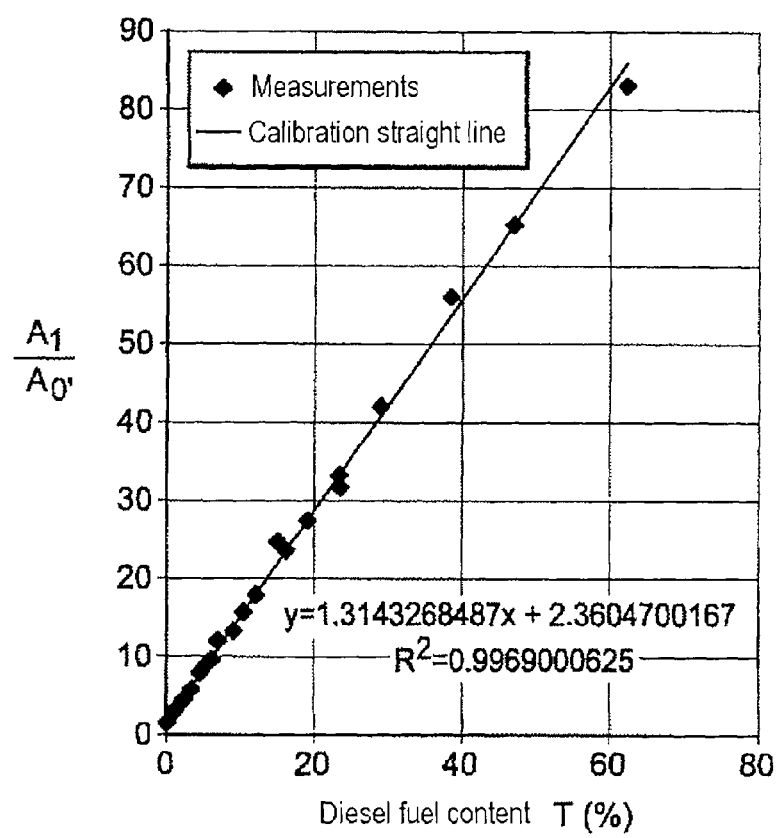
FIG. 3 illustrates an example of a calibration straight line.

The corrected area A0' is calculated as follows:

The weight of pentane is $m_4-m_3$. The concentration of pentane is then $[C_5]=(m_4-m_3)/m_4$. Taking $[C_i]$ to be the imposed concentration (for example, 0.0066), Thus: A0'=A0*$[C_i]$/$[C_5]$ The establishment of the calibration curve is carried out in the following way:

the weighed real content of diesel fuel is g=$(m_2-m_1)/m_2$;

for each area Ai, with i between 1 and 4, the straight line corresponding approximately to the function $$f(g) = \left(\sum_{k=l}^{i} Ak\right) / A0'$$

is plotted, for example by the least squares method. Expressing the equation of the straight line in the form $y=a_i x+b_i$, the values of $a_i$ and $b_i$ are determined. 4 calibration straight lines are thus obtained from the same standards. An example of points and of a calibration curve are given in FIG. 3.

For a sample to be analyzed, the integrations are carried out in a similar manner, in order to determine the areas A0', A1, A2, A3 and A4. For i between 1 and 4, the ratios $$\left(\sum_{k=l}^{i} Ak\right) / A0'$$

are then calculated.

Based on the ratios obtained and on the calibration straight lines, the content of diesel fuel is determined by means of the following formula:

$$\left(\left(\left(\sum_{k=l}^{i} Ak\right) / A0'\right) - b_i\right) / a_i$$

If the lubricant is known, only the calculation of diesel fuel content for i=1 is taken into account.

For certain oils which are not very superimposed with the heavy constituents of the diesel fuel, the result to be taken into account is determined according to the content of diesel fuel obtained for i=1. For example, if this value is between 0 and 2%, the value obtained for i=1 is taken into account; if this value is between 2 and 10%, the value obtained for i=2 is taken into account; if this value is between 10 and 20%, the value for i=3 is taken into account; if this value is greater than 20%, the value for i=4 is taken into account. The co-elution of the diesel fuel is then taken into account.

Since certain oils may have a specific structure (for example, when C16 is present in the base mixture), a specific integration may be required. Such an integration may in particular exclude the area of the peak corresponding to the compound in question and require a specific calibration.

Advantageously, the temperature profile and the pressure profile of the chromatograph are corrected periodically according to standards effected on a solution containing the $C_5$, $C_{20}$-$C_{26}$ and $C_{30}$ hydrocarbons. For example, $C_5$, $C_{20}$-$C_{26}$ and $C_{30}$ alkanes may be used with, for example, 60 mg of each of these compounds per 5 ml of $CS_2$. Wearing of the column and the change in retention times are thus taken into account.

Advantageously, new calibration straight lines are produced for each new column used in the chromatograph.

This method makes it possible to separate the oil from the diesel fuel by separating their $C_n$ hydrocarbons, n ranging from 6 to 50, a hydrocarbon grouping together a family of saturated and/or unsaturated compounds. This method is not a compound-by-compound separation, but a separation of family of hydrocarbon-based compounds (saturated and/or unsaturated) by a family of hydrocarbon-based compounds (saturated and/or unsaturated).

The invention claimed is:

1. A method for determining proportion of diesel fuel in a lubricating oil of a combustion engine, comprising:

forming a mixture containing a sample of lubricating oil to be analyzed and a $C_5$ hydrocarbon or a $C_5$ alkane according to a predetermined proportion;

injecting the mixture into an injector of a gas chromatograph;

establishing a chromatogram of the sample to be analyzed;

determining a first parameter M representative of the area of a peak of the chromatogram associated with the $C_5$ hydrocarbon or the $C_5$ alkane;

determining a second parameter C representative of the area of at least one peak of the chromatogram associated with a hydrocarbon representative of the diesel fuel; and determining the proportion T of diesel fuel of the sample to be analyzed, by formula:

$$T = \frac{C/(M) - b}{a}$$

in which a and b are constants defining equation $y=ax+b$ of a calibration straight line of the ratio between the second and the first parameters as a function of the proportion of diesel fuel.

2. The method as claimed in claim 1, in which the second parameter C is representative of the area of at least one peak of the chromatogram associated with a hydrocarbon in the $C_6$ to $C_{25}$ group.

3. The method as claimed in claim 2, in which an approximation of the content of diesel fuel is calculated as a function of a third parameter C' representative of the area of a peak associated with a $C_{20}$ hydrocarbon of the chromatogram, and then a corrected diesel fuel content is calculated as a function of a fourth parameter C" representative of the area of plural peaks associated with respective hydrocarbons chosen from the $C_{20}$ to $C_{25}$ group, the number of these peaks being a function of the approximation calculated.

4. The method as claimed in claim 2, in which the second parameter C is representative of the area of plural peaks associated with respective hydrocarbons chosen from the $C_{20}$ to $C_{25}$ group.

5. The method as claimed in claim 1, in which the second parameter C is established by formula: $C=\alpha \cdot C0/[C_5]$, with C0 being the area of the peak associated with the $C_5$ hydrocarbon or the $C_5$ alkane, $\alpha$ being a coefficient of correction to a reference concentration, and $[C_5]$ being the concentration of the $C_5$ hydrocarbon or $C_5$ alkane in the sample.

6. The method as claimed in claim 1, wherein the mixture formed comprises carbon disulfide in a predetermined proportion.

7. The method as claimed in claim 1, further comprising a prior operation of determining the equation of the calibration straight line during which:

plural standard mixtures comprising a lubricating oil and diesel fuel according to distinct predefined proportions, and the $C_5$ hydrocarbon or the $C_5$ alkane according to a predetermined proportion, are formed;

for each standard mixture:
injecting the standard mixture into the injector of the gas chromatograph;
establishing a chromatogram of the standard mixture;
determining a parameter M0 representative of the area of a peak of the chromatogram associated with the $C_5$ hydrocarbon or the $C_5$ alkane; and
determining a parameter C0 representative of the area of a peak of the chromatogram associated with a hydrocarbon representative of the diesel fuel; and based on the pairs of first and second parameters obtained for the various standard mixtures, determining the parameters a and b of the calibration straight line.

8. The method as claimed in claim 1, in which the chromatogram is established by a flame ionization detector, and in which a calculation member carries out integrations of the chromatogram so as to calculate the area of each peak of the chromatogram.

* * * * *